United States Patent [19]

Forman

[11] Patent Number: 4,919,382

[45] Date of Patent: Apr. 24, 1990

[54] MULTI-POST YOKE GIMBAL

[75] Inventor: Donald B. Forman, San Diego, Calif.

[73] Assignee: The United States of America as represented by the Secretary of the Navy, Washington, D.C.

[21] Appl. No.: 244,363

[22] Filed: Sep. 14, 1988

[51] Int. Cl.$^5$ .............................................. B25J 17/02
[52] U.S. Cl. ........................... 248/178; 248/DIG. 13; 248/487; 74/479; 74/89.15; 901/23
[58] Field of Search ............... 248/178, 179, 181, 184, 248/DIG. 13, 182, 487; 74/479, 89.15; 901/23, 24, 28, 29

[56] References Cited

U.S. PATENT DOCUMENTS

| | | | |
|---|---|---|---|
| 3,215,391 | 11/1965 | Storm | 248/179 X |
| 3,288,421 | 11/1966 | Peterson | 248/179 X |
| 4,607,578 | 8/1986 | Inoue et al. | 248/179 X |
| 4,790,718 | 12/1988 | Vickers | 901/23 X |
| 4,806,068 | 2/1989 | Kohli et al. | 74/479 X |
| 4,819,496 | 4/1989 | Shelef | 74/479 |

FOREIGN PATENT DOCUMENTS 1224137 4/1986 U.S.S.R. .................. 901/23

Primary Examiner—Ramon S. Britts
Assistant Examiner—Karen J. Chotkowski
Attorney, Agent, or Firm—Harvey Fendelman; Thomas G. Keough

[57] ABSTRACT

A multi-post gimbal mechanism for imparting motion to an object about a center of rotation including a frame for supporting the object and a plurality of elongated posts coupled to the frame so as to permit orbital rotation of the frame about each of the coupling points. Each of the elongated posts is selectively adjustable in position and drive means are coupled to the elongated posts to selectively adjust the position. The drive means are supported on a mounting base and are pivotally attached to the mounting base such that each drive mechanism can rotate about an axis that is orthogonal to the longitudinal axis of its corresponding elongated support post.

12 Claims, 3 Drawing Sheets

MULTI-POST YOKE GIMBAL

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates generally to the field of gimbal type devices and to the field of devices for providing two orthogonal degrees of freedom to a load device. More particularly, the present invention is related to the field of servo controlled, rate stabilizing platforms for sensor systems which are particularly suitable for use for guidance systems such as missile guidance systems and surveillance systems for data/intelligence gathering and target tracking. While the present invention is particularly suitable for such applications, the present invention relates more generally to the field of positioning systems and may be utilized anywhere that an object or device requires orientation and repositioning from one position to another.

Traditionally, stabilized sensor platforms have been very high cost systems due to the fact that they are intricate and complex mechanical structures. Stabilized missile sensors require at least two degrees of freedom of movement (azimuth and elevation). These two degrees of freedom of movement have been accomplished in the past by an inner/outer gimbal arrangement of the stabilized platform. In an improved arrangement as is shown, for instance, in U.S. Pat. No. 4,324,378 the inner gimbal torque motor is secured to the outer gimbal ring to permit increased weight and volume sensors to be packaged and located at the center of rotation of the gimbal axis. A problem with the gimbal arrangement disclosed in the aforementioned patent is that the nodal point of an antenna system mounted on the platform cannot be positioned at the center of the axis of rotation of the antenna system due to the fact that the center of rotation of the gimbal is located in a space occupied by the platform. Further, the platform is driven by a gear arrangement which must be affixed to the platform itself thereby further precluding positioning of the antenna nodal point at the center of the axis of rotation.

Another positioning device useable for positioning an antenna or other bore-cited device in azimuth and elevation is disclosed in U.S. Pat. No. 3,215,391. The device disclosed in that patent requires utilization of U-joints in the extendable supports in order to achieve spherical rotation capability of the platform. This type of arrangement suffers from inherent instability. For this reason such devices are not acceptable for utilization in many applications such as missile guidance.

Other prior art gimbal designs suffer from lack of space requirements for electronics and hardware within the platform and also lack of symmetry about the rotation axes.

SUMMARY OF THE INVENTION

The present invention overcomes the previously described disadvantages of the prior art. This is accomplished by the provision of a gimbal platform that may be open at its center and the center of which corresponds exactly with the center of the axis of rotation. Accordingly, where the present invention is used as a stabilized platform in a missile sensor application, the nodal point of the antenna device mounted on the platform may coincide exactly with the center of axis of rotation of the platform. By making the center of the platform of the present invention open, a further advantage is achieved in that the wiring for the electronics or device that is mounted on the platform can be drawn through the center of the platform without the need for routing the wiring around the periphery of the platform.

The present invention, therefore, is primarily suitable for use as a servo controlled, rate stabilized sensor platform for use in missile guidance systems or the like but as stated above may be utilized as a positioning device in any application where positioning in azimuth and elevation of a mounting surface with respect to some other surface in response to servo controls is required.

The advantages of the present invention generally are accomplished by providing an annular shaped frame for supporting an object or device to be positioned. A plurality of elongated screw driven or hydraulically driven posts are each coupled to the support frame with an orbital type coupling mechanism that permits each post to rotate orbitally with respect to the support frame. The posts are selectively adjustable in position, i.e. length by a controllable drive that is used to adjust the relative position of the coupling point of the elongated posts and the support frame to a mounting base or other reference.

OBJECTS OF THE INVENTION

Accordingly, it is the primary object of the present invention to disclose a gimbal platform that provides improved utilization of space.

It is another object of the present invention to disclose a gimbal mechanism that is symmetrical is design.

A still further object of the present invention is to disclose a gimbal mechanism in which the center of rotation is open such that the nodal point of an antenna can be positioned there.

These and other objects of the invention will become more readily apparent from the ensuing specification when taken with the appended claims and the attached drawings.

DESCRIPTION OF THE PREFERRED EMBODIMENT

Figure 1:
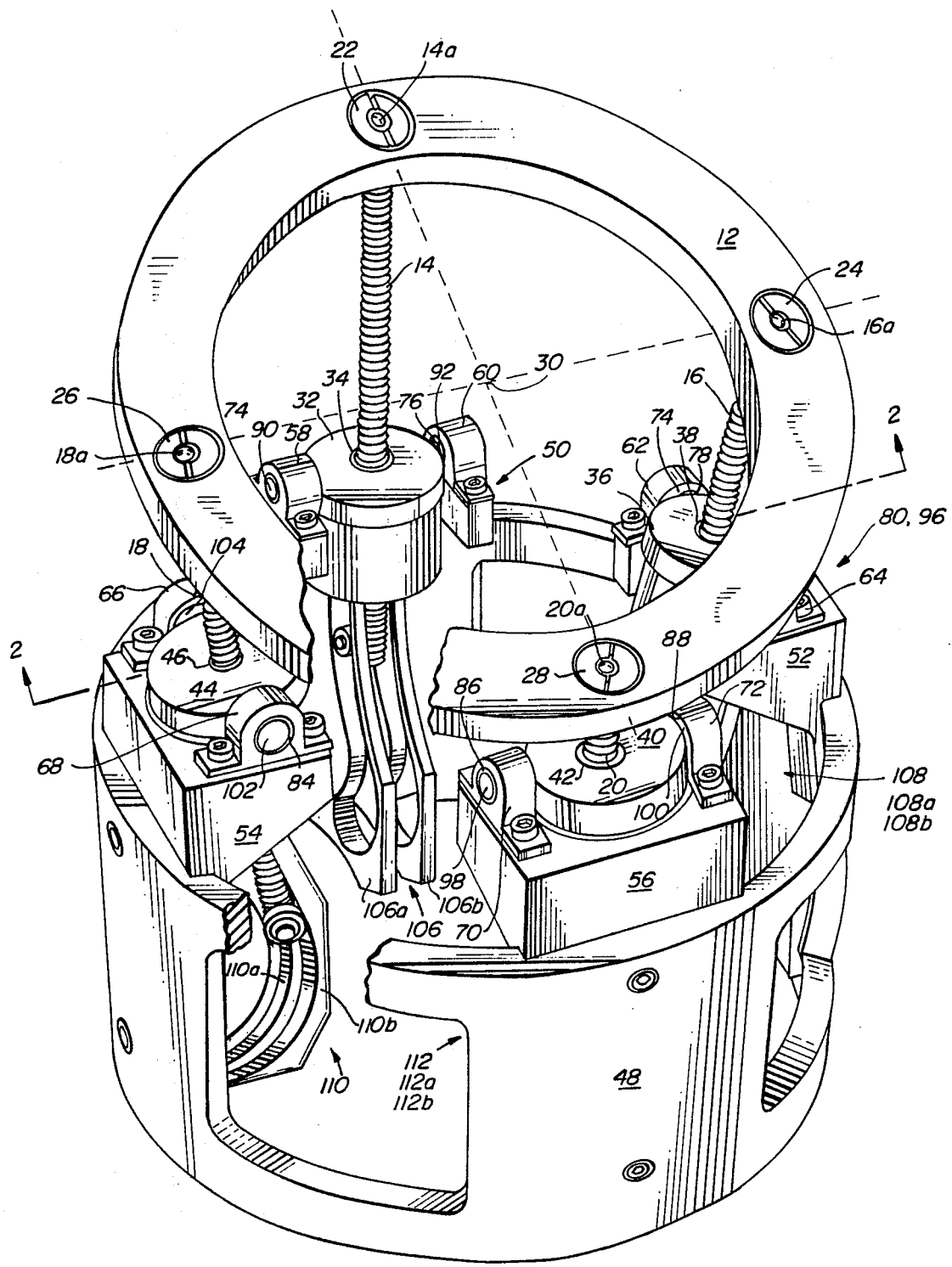
FIG. 1 is a partially cut away perspective view of the multi-post gimbal of the present invention.
Figure 2:
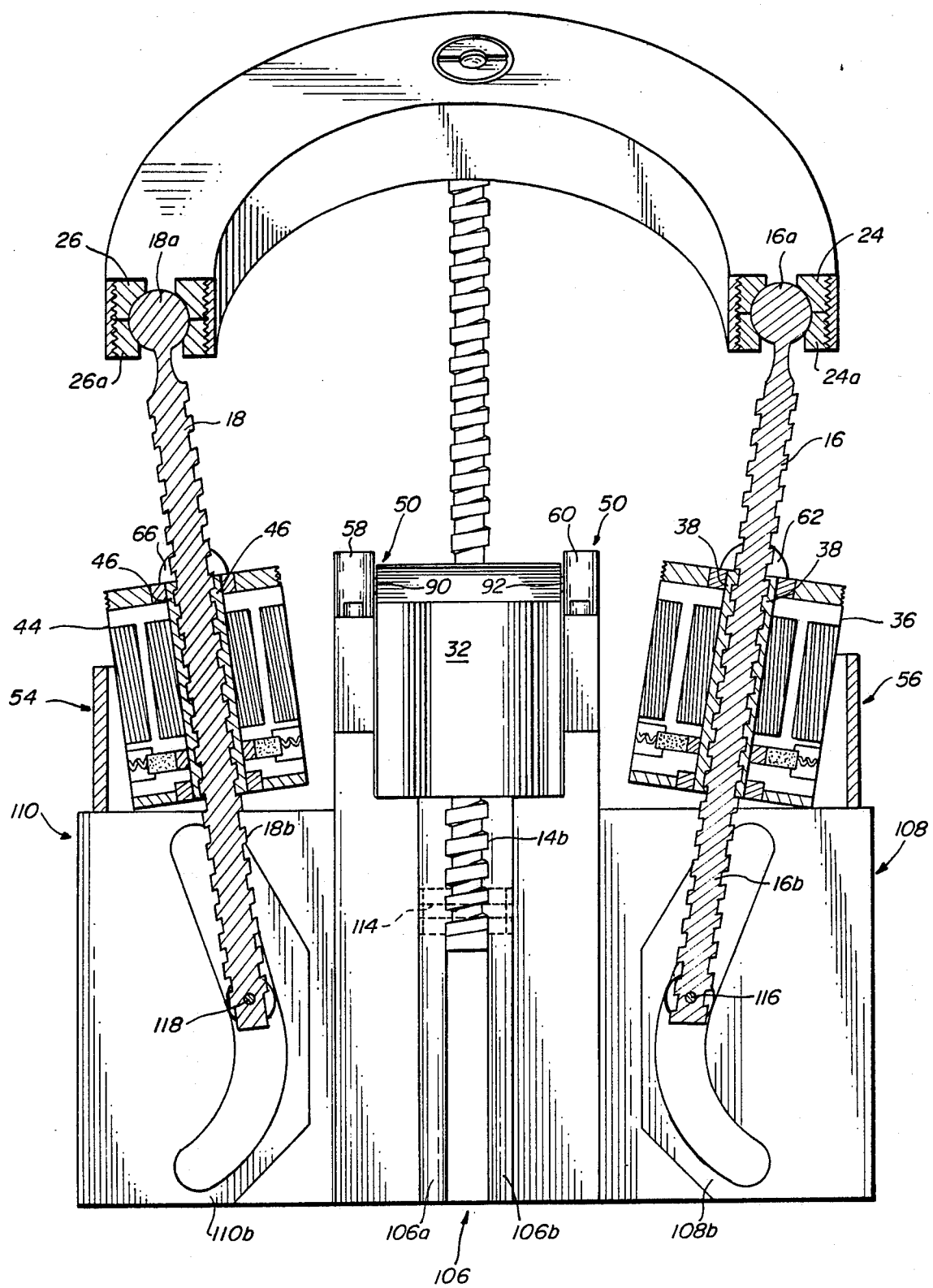
FIG. 2 is a top view of the multi-post gimbal mechanism of the present invention.
Figure 3:
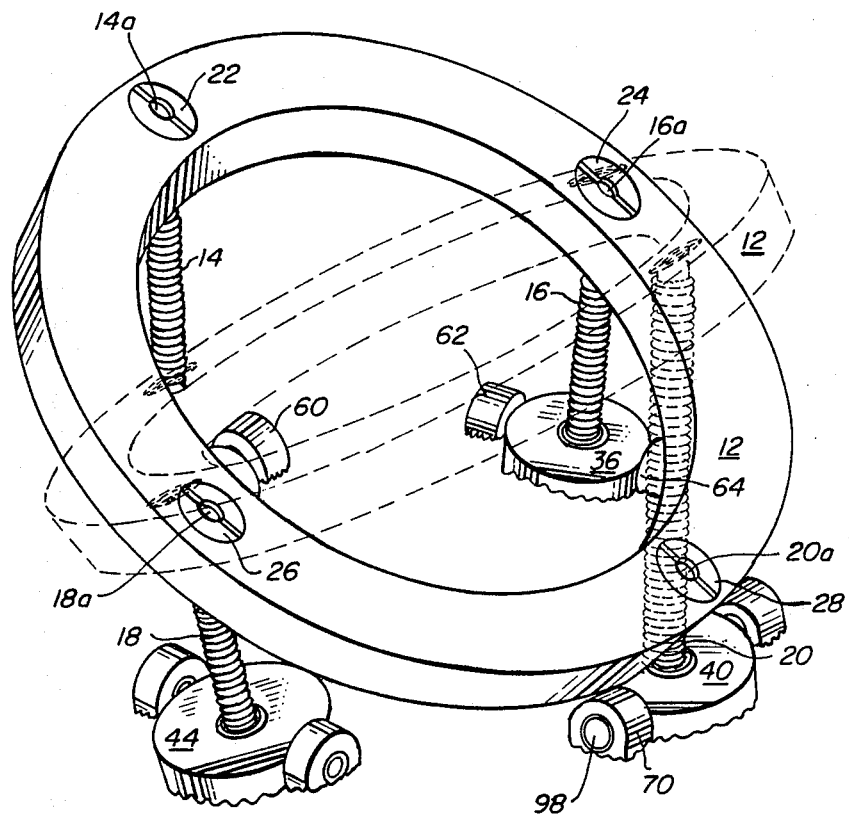
FIG. 3 is a cross-section of the gimbal mechanism of the present invention taken along lines III—III of FIG. 2.

Referring now collectively to FIGS. 1, 2 and 3 the multi-post yoke gimbal mechanism of the present invention will be described. The device or object (not shown) to be positioned by the mechanism of the present invention is mounted on support frame or yoke 12. While support frame 12 is illustrated and described herein as being annular is shape, it is to be understood that it is within the scope of the present invention that other shapes may be utilized as desired. For instance, any closed, multi-sided figure such as a hexagon or square may also be utilized depending upon the design requirements. The orientation of the support frame 12 is selectively positionable by means of a plurality of elongated posts 14, 16, 18 and 20. It is to be understood that although the embodiment of the present invention illustrated in FIGS. 1, 2 and 3 is illustrated and described herein as including four elongated posts for positioning the frame, other numbers of posts may be utilized. As few as two posts may be utilized or any other number greater than two may also be utilized within the scope of the present invention.

The top ends of each of the elongated posts 14, 16, 18 and 20 are terminated in ball type bearings 14A, 16A, 18A and 20A. The ball type bearings 14A, 16A, 18A and 20A are coupled to frame 12 by means of socket type bearing seats 22, 24, 26 and 28. The socket type bearing seats 22, 24, 26 and 28 may be threaded on their outer periphery for engagement with mating threaded surfaces formed in the support ring 12. The lower halves of the bearing seats 22, 24, 26 and 28 are placed over support posts 14, 16, 18 and 20 prior to coupling of the support posts with the support frame 12 and are then threaded into the mating threaded aperture in the support frame 12 as would readily be understood. Bearing seat lower halves 24a and 26a are shown in FIG. 2. As can be appreciated, the bearing/socket coupling of the elongated posts 14, 16, 18 and 20 to the support frame 12 provided by the above described bearings and socket type bearing seats enables the coupling point of each of the elongated posts 14, 16, 18 and 20 to the support frame 12 to move orbitally at the coupling point.

It should be readily appreciated that any desired load or object which is to be positioned by the present invention can be inserted within the space encompassed by support frame 12. Because of this, it should also be readily appreciated that, in an application of the present invention in which the load supported by support frame 12 comprises an array of antennas having a bore site and a nodal point, the nodal point can be positioned exactly within the geometric center 30 of the support frame 12.

In the preferred embodiment of the present invention, each of the elongated support posts 14, 16, 18 and 20 comprises a shaft that is threaded so that its position can be selectively adjusted by means of servo control motors. In the illustrated embodiment of the present invention four electric servo control motors are utilized. Motor 32 includes motor armature 34. The armature 34 has a threaded interior passageway extending therethrough which is in threaded, mating engagement with the exterior threaded surface of post 14 as is illustrated. Similarly, motor 36 includes armature 38 having an interior threaded passageway which is in threaded, mating engagement with the exterior threaded surface of post 16. Motor 40 includes armature 42 which has a threaded interior passageway that is in threaded, mating engagement with the exterior surface of post 20. Likewise, motor 44 includes armature 46 which has an interior threaded passageway that is in threaded, mating engagement with the exterior threaded surface of post 18.

The gimbal mechanism of the present invention, by way of example only, includes base support member 48 which in the illustrated embodiment is generally cylindrically shaped. Four motor mounts 50, 52, 54 and 56 are suitably attached to base support 48 at symmetrical positions along the base support 48 as is illustrated in FIG. 1. Each motor mount 50, 52, 54 and 56 includes a pair of bearing blocks 58 and 60, 62 and 64, 66 and 68, and 70 and 72, respectively. Each bearing block 58, 60, 62, 64, 66, 68, 70 and 72 has an inner bearing surface formed therein, namely 74, 76, 78, 80, 82, 84, 86, and 88, respectively. Bearing shafts 90 and 92 are attached to motor 32 and have journaled outer surfaces which are engaged with bearing surfaces 74 and 76, respectively, to permit motor 32 to rotate around the longitudinal axes of shafts 90 and 92. Similarly, bearing shafts 94 and 96 are attached to motor 36 and have journaled outer ends which mate with bearing surfaces 78 and 80 to permit motor 36 to rotate around the longitudinal axes of shafts 94 and 96. Likewise, bearing shafts 98 and 100 are attached to motor 40 and have journaled outer ends which are engaged with bearing surfaces 86 and 88 to permit motor 40 to rotate around the longitudinal axes of shafts 98 and 100. In a like manner shafts 102 and 104 are attached to motor 44 and have journaled outer ends which are engaged with bearing surfaces 82 and 84 to permit motor 44 to rotate around the longitudinal axes of shafts 102 and 104.

Base support 48 also includes lower post support members 106, 108, 110 and 112. Each of the lower post support assemblies 106, 108, 110 and 112 includes an identical pair of arcuate shaped channel members 106a and 106b, 108a and 108b, 110a and 110b, and 112a and 112b, respectively.

Bearing assembly 114 is attached to lower end 14b of post 14 by suitable means such as threaded coupling as would be readily understood by those of ordinary skill in this art. Similarly, bearing assembly 116 is attached to lower end 16b of post 16, bearing assembly 118 is attached to lower end 18b of post 18 and a bearing assembly (not shown) is attached to the lower end of post 20. The four bearing assemblies are positioned in slidable engagement with the arcuate channels formed by the lower post support pairs described above as is illustrated in FIGS. 1 and 3. The lower post supports, bearing assemblies and arcuate channels therein are used for increasing the stability of the gimbal mechanism of the present invention.

The gimbal mechanism of the present invention operates as follows. In order to reposition support frame 12 so that the z-axis, i.e. the axis that is orthogonal to the plane of the support frame 12 and that extends from the geometric center of the support frame 12, signals are provided to motors 32, 36, 40 and 44 to either advance the threaded posts 14, 16, 18, or 20 upwards or to draw them downwards. For instance, posts 16 and 18 could remain stationary while post 14 is extended upwards by a distance that is equal to the distance that post 18 is drawn downwards. As a further example, while posts 14 and 20 are being so adjusted, posts 16 and 18 could similarly be adjusted whereby post 16 would be extended upwards by a distance equal to the distance that post 18 is drawn downwards. Such repositioning and repointing of support frame 12 is facilitated by reason of the fact that the coupling point of each of the posts to the support frame is free to rotate orbitally and also by the fact that each of the motors is free to rotate around the longitudinal axis of its respective support shaft. In the embodiment of the present invention in which additional stability is achieved by using the lower post support/bearing assemblies including the involute/arcuate channels illustrated and described above, the lower post ends travel in the path defined by the respective involute or arcuate channel.

While the preferred embodiment of the present invention has been illustrated and described as including jack post or threaded post type assemblies, it is to be understood that it is within the scope of the present invention that other post and post drive assemblies could be utilized. For instance, hydraulic or pneumatically driven ram assemblies could be used in place of the jack posts and motor drive assemblies.

Obviously, many modifications and variations of the present invention are possible in the light of the above teachings. It is therefore to be understood that within the scope of the appended claims the invention may be practiced otherwise than as specifically described.

I claim:

1. A multi-post gimbal mechanism for imparting motion to an object about a center of rotation comprising:
   a frame for supporting said object;
   a plurality of elongate posts, each coupled to said support frame at a coupling point so as to permit orbital rotation of said frame about each said coupling point, each of said elongate posts being selectively adjustable in position;
   drive means coupled to said plurality of elongate posts for selectively adjusting the position of each of said elongate posts;
   a mounting base, said drive means being connected to said mounting base;
   each of said elongate posts including a first end and a second end, each said first end being connected at said coupling point; and
   said mounting base including a plurality of arcuate guides connected thereto, the second end of each of said elongate posts being positioned in one of said plurality of arcuate guides.

2. The multi-post gimbal mechanism of claim 1 wherein each said coupling point of each of said elongate posts to said support frame comprises an orbital socket.

3. The multi-post gimbal of claim 2 wherein:
   each said orbital socket comprises a bearing seat and a substantially spherical bearing substantially contained within said bearing seat and connected to an end of one of said plurality of elongate posts.

4. The multi-post gimbal of claim 1 wherein:
   said frame has a geometric center; and
   said drive means is coupled to said mounting base such that said geometric center of said frame is the same as said center of rotation and is stationary with respect to said mounting base during said selective positioning of each of said elongate posts.

5. The multi-post gimbal of claim 1 wherein:
   said drive means comprises a plurality of drive mechanisms, each of said drive mechanisms being operably coupled to one of said plurality of elongate posts for selectively adjusting the length of said post between said drive mechanism and said frame.

6. The multi-post gimbal mechanism of claim 5 further comprising:
   means for pivotally mounting each of said drive mechanisms to said mounting base so as to permit each said drive mechanism to rotate with respect to said mounting base.

7. The multi-post gimbal mechanism of claim 6 wherein:
   each of said drive mechanisms has an axis of rotation relative to said base; and
   the longitudinal axis of each said elongate post is orthogonal to said axis of rotation of each of said drive mechanisms.

8. The multi-post gimbal mechanism of claim 6 wherein:
   each said drive mechanism comprises:
   an electric motor having an armature;
   said armature having a threaded interior passageway extending therethrough; and
   each of said plurality of elongate posts has a threaded exterior surface in threaded engagement with one of said threaded interior armature passageways.

9. The multi-post gimbal mechanism of claim 8 wherein:
   a bearing is coupled to each said second end and cooperates with one of said arcuate guides for providing freedom of motion of said second end within said arcuate guide.

10. The multi-post gimbal mechanism of claim 9 wherein each said coupling point of each of said elongate posts to said support frame comprises an orbital socket.

11. The multi-post gimbal mechanism of claim 10 wherein:
    each said orbital socket comprises a bearing seat and a substantially spherical bearing substantially contained within said bearing seat and connected to an end of one of said plurality of elongate posts.

12. The multi-post gimbal mechanism of claim 8 wherein:
    a bearing is coupled to each said second end and cooperates with one of said arcuate guides for providing freedom of motion of said second end within said arcuate guide.

* * * * *